United States Patent [19]

Kellie et al.

[11] Patent Number: 4,532,723

[45] Date of Patent: Aug. 6, 1985

[54] OPTICAL INSPECTION SYSTEM

[75] Inventors: Truman F. Kellie, Westchester, Ohio; J. David Landry, Wilmington, N.C.; Ching C. Lai, Pleasanton, Calif.

[73] Assignee: General Electric Company, San Jose, Calif.

[21] Appl. No.: 361,992

[22] Filed: Mar. 25, 1982

[51] Int. Cl.³ .................... G01N 21/89; G01B 11/10; G01B 11/30

[52] U.S. Cl. .................................... 356/73; 209/579; 209/587; 356/237; 356/385

[58] Field of Search ................ 356/73, 371, 384, 385, 356/386, 445, 237; 250/572; 209/579, 586, 587

[56] References Cited

U.S. PATENT DOCUMENTS

| | | | |
|---|---|---|---|
| 3,826,576 | 7/1974 | Stewart | 356/384 |
| 3,874,798 | 4/1975 | Antonsson et al. | 356/386 |
| 3,947,129 | 3/1976 | Wiklund | 356/385 |
| 4,074,938 | 2/1978 | Taylor | 356/386 |
| 4,197,888 | 4/1980 | McGee et al. | 356/384 X |
| 4,253,768 | 3/1981 | Yaroshuk et al. | 356/431 |
| 4,349,112 | 9/1982 | Wilks et al. | 250/223 R |
| 4,410,278 | 10/1983 | Makihira et al. | 356/445 |

*Primary Examiner*—Vincent P. McGraw

*Attorney, Agent, or Firm*—Ivor J. James, Jr.; Samuel E. Turner; Raymond G. Simkins

[57] ABSTRACT

An optical inspection system is disclosed which determines surface and other features of objects by illuminating them with a light beam having substantially uniform light intensity in space and time. The light beam is derived from a light source whose light intensity may vary in space and time. The surface features of each object are inspected by detecting light reflected from the object through a lens system which focuses the reflected light on an array of photosensitive elements. The output signals provided by the array may be used to provide a measure indicative of the conformance of the inspected surface to predetermined criteria. The inspection system is further capable of determining other features of the inspected object, such as the height of the object, by illuminating the object with a second light beam derived from a second light surface. A portion of the second light beam is eclipsed by the object and the non-eclipsed portions are directed to a second array of photosensitive elements to provide signals indicative of the desired dimension.

1 Claim, 12 Drawing Figures

FIG. 2
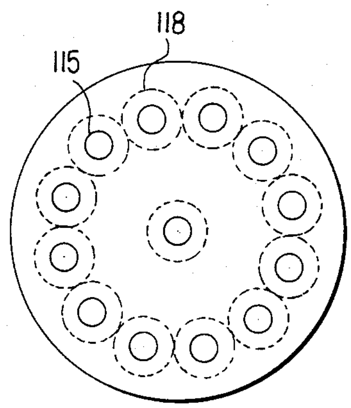
FIG. 3
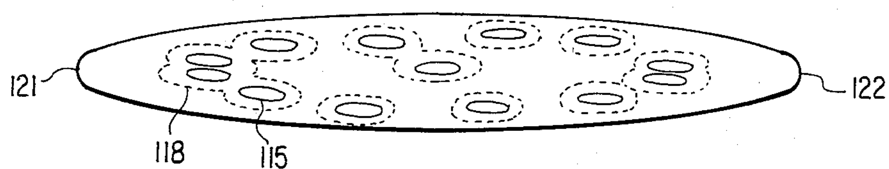
FIG. 4
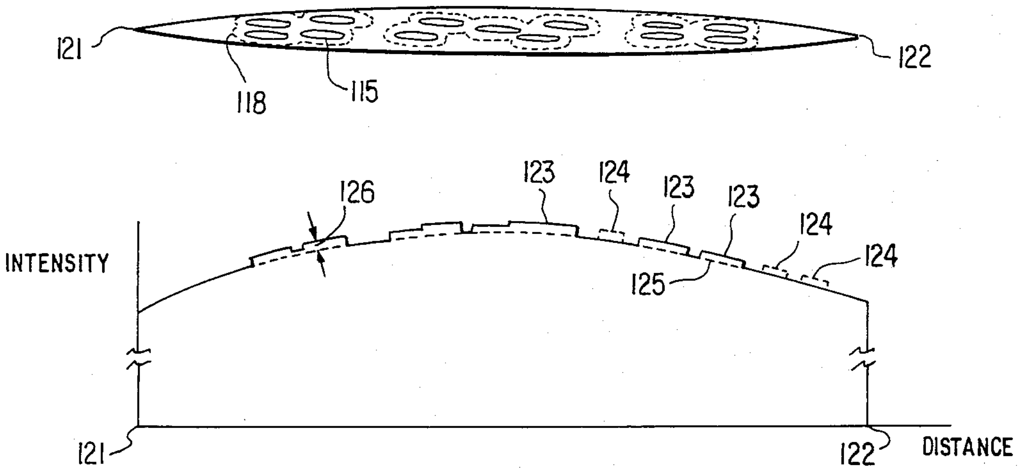
FIG. 5

FIG. 9
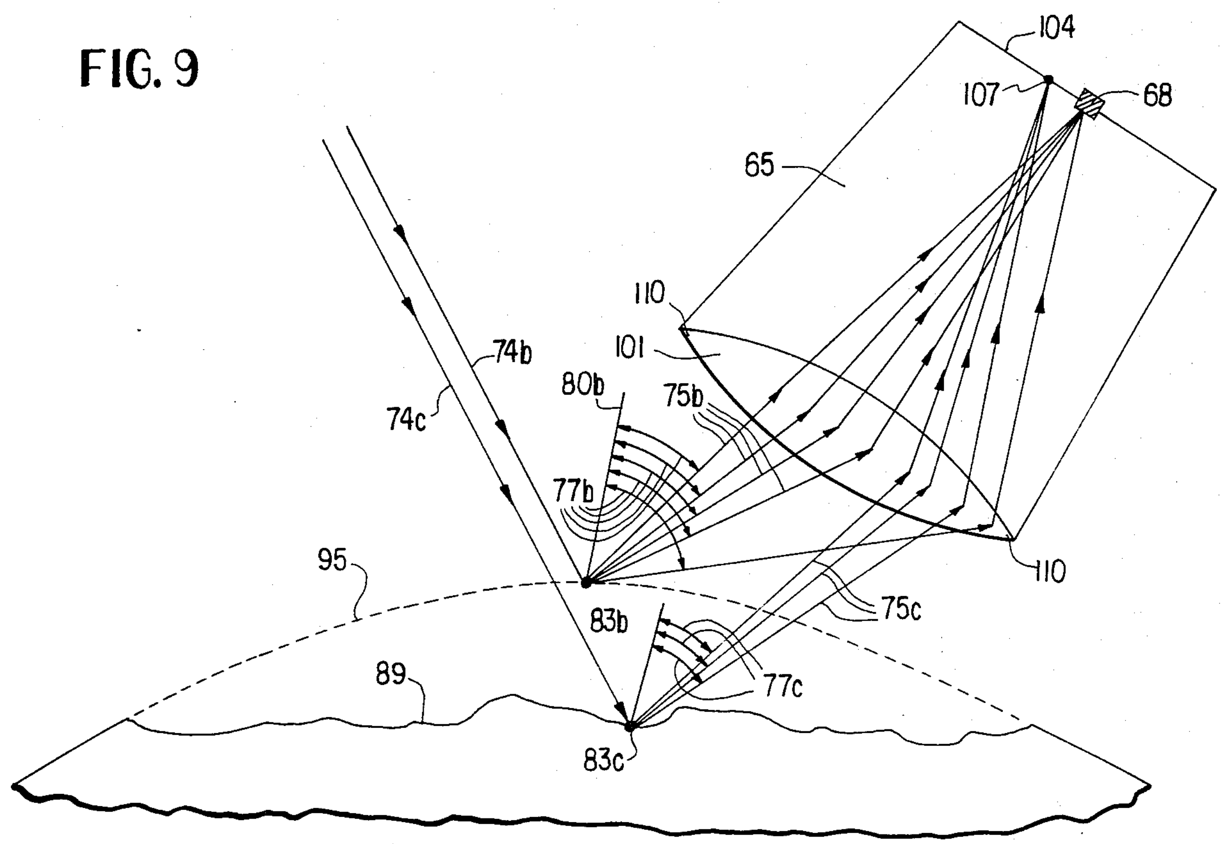
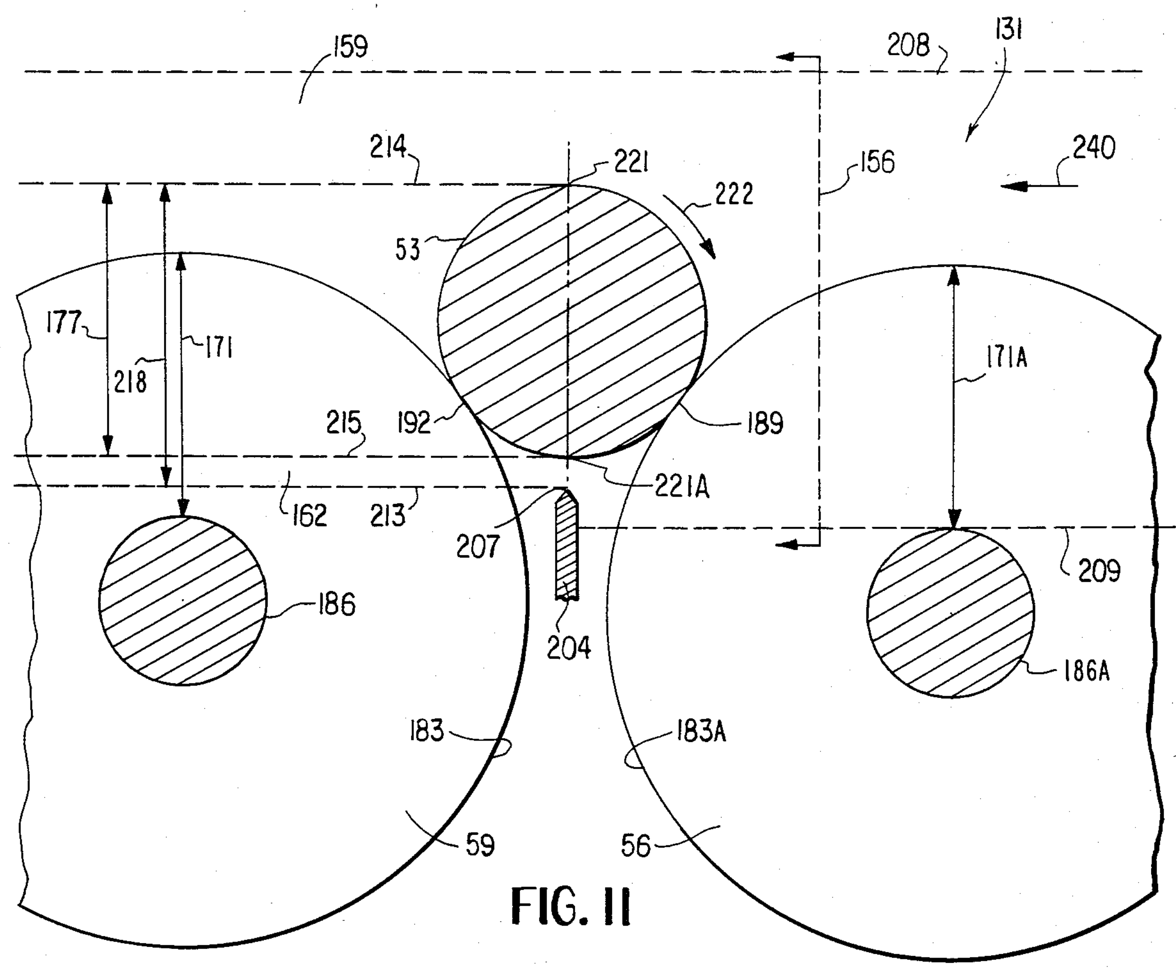
FIG. 11

FIG. 10
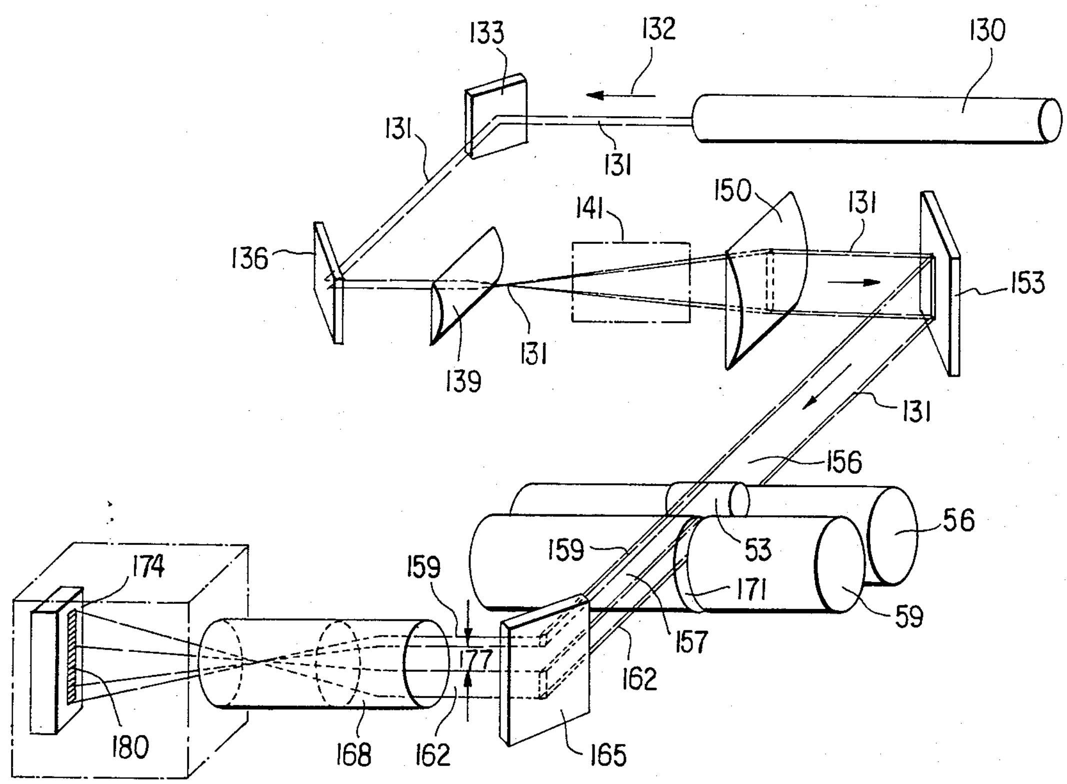
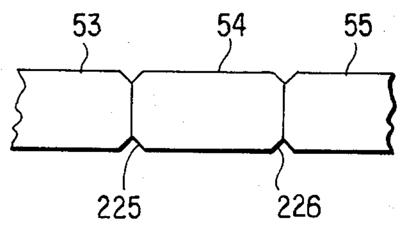
FIG. 12

OPTICAL INSPECTION SYSTEM

The present invention relates in general to optical inspection systems and in particular to a system for optically inspecting the surface and at least one transverse dimension of an object by providing regions of illumination of substantially uniform light intensity, notwithstanding the fact that the light intensity at the light source may vary across the cross section of the light beam, as well as varying with time.

CROSS REFERENCE TO RELATED APPLICATIONS

The following applications are respectively incorporated by reference herein:

"Transport Apparatus", Frederick C. Schoenig, Jr., J. David Landry, Edward S. Walker and Ching C. Lai, Ser. No. 361,993, filed Mar. 25, 1982;

"Tray Loader Method and Apparatus for Nuclear Fuel Pellets", Harold Bleckley King, Ching Chung Lai and Edward Samuel Walker, Ser. No. 362,046, filed Mar. 25, 1982;

"Automated Inspection System", Frederick C. Schoenig, Jr., Leonard N. Grossman, Ching C. Lai, William Masaitis, Robert O. Canada, Ser. No. 361,933, filed Mar. 25, 1982.

BACKGROUND OF THE INVENTION

For certain types of manufactured objects it is advantageous to inspect the object for conformance to predetermined criteria without contacting the inspected objects. For example, nuclear pellets for fuel rods must be inspected following grinding for the presence of surface defects, for conformance to predetermined dimensions and for other anomalies which may adversely affect the performance of the pellets in the rod. To avoid contact with the cylindrical pellets an optical inspection may be made, preferably by means of a system whereby the entire process is automated. In order to inspect the cylindrical surface of the object of interest, a beam of light is projected onto the surface an photosensitive elements are utilized to detect light which is reflected back from the surface of the object. The photosensitive elements produce output signals representative of the amount of the reflected light incident thereon. Variations in these output signals are interpreted as corresponding to variations in the surface features of the object.

One requirement for the proper functioning of such apparatus is that the variations in the intensity of reflected light be produced only by the surface features of the object, rather than by variations of the intensity of light which illuminates the object. Such light sources as are commonly available for the intended purpose do not, as a rule, meet this requirement because the intensity distribution of the light provided often exhibits variations across the cross section of the light beam, as well as variations with time.

Another problem connected with this type of optical inspection technique arises from variations in the intensity of reflected light caused by variations in the reflective properties of the inspected object. Thus, a light beam reflected by a smooth surface which is shiny (that is, specular) travels substantially in a single direction away from the point, or locus, of reflection on the surface. There is relatively little scattering of light in random directions and thus a large proportion of the reflected light, commonly termed specularly reflected light, will reach the photosensitive elements. However, when a light beam is reflected by a smooth surface which is dull (that is, diffuse), more scattering of light in random directions will occur and less of the reflected light, termed diffusely reflected light, will reach the photosensitive elements.

When a light beam is reflected by a surface which is rough rather than smooth, i.e. a surface which contains irregularities such as cracks or pits, light will to a large extent be reflected in random directions, and it can be specularly or diffusely reflected. Here, the loci of reflection are no longer located on the surface, but at the walls and floor of the cracks or pits. These loci are randomly oriented and hence light is reflected in random directions. Thus, less light will be reflected to the photosensitive elements than even for a dull surface. In order for the inspection apparatus to operate effectively, it must be capable of distinguishing between the different types of conditions outlined above. Further, it must do so on a continuing basis since different surface areas will be inspected as the object advances past a viewing field.

A further requirement of optical inspection apparatus of the type under discussion, is that light be utilized in an efficient manner. Two types of light source are commonly employed, incandescent and coherent, and both provide light of relatively low intensity. Although high intensity incandescent light sources are available, they produce excessive heat which may be undesirable in the context of the inspection procedure. On the other hand, high intensity coherent light sources are prohibitively expensive. Thus, inasmuch as practical considerations dictate the use of low intensity light sources, light loss must be avoided by efficiently collecting reflected or transmitted light and directing it to the photosensitive elements. Further, the light beam must be properly focused to illuminate only the region which is viewed by the photosensitive elements. For a linear array of elements, such a region must therefore be linear.

OBJECTS OF THE INVENTION

It is a primary object of the invention to provide apparatus for optically inspecting the surface and other features of objects, which avoids the disadvantages of prior art equipment of this type.

It is another object of the present invention to provide new and improved optical inspection apparatus wherein the light projected onto the region of illumination of the object under examination has a substantially uniform intensity distribution throughout the region of illumination.

It is a further object of the present invention to provide new and improved inspection apparatus which is capable of providing a substantially uniform light intensity distribution in the region of illumination, notwithstanding the use of a spatially non-uniform light source.

It is still another object of the present invention to provide new and improved optical inspection apparatus which is capable of providing a substantially uniform light intensity distribution in the region of illumination, notwithstanding the use of a light source whose light intensity distribution may vary with time.

It is still a further object of the present invention to provide new and improved optical inspection apparatus which is capable of providing a substantially uniform light intensity distribution throughout an elongate region of illumination having a large length-to-width ratio.

It is yet a further object of the present invention to provide new and improved optical inspection apparatus which is capable of distinguishing between light reflected from either a smooth surface, a dull surface, or a rough surface.

It is yet another object of the present invention to provide new and improved optical inspection apparatus wherein the capture of light reflected by the object under examination is maximized.

It is yet another object of the present invention to provide new and improved optical inspection apparatus wherein a dimension, such as the height of the cross sectional image of the inspected object may be measured.

The foregoing and other objects of the present invention, together with the features and advantages thereof, will become apparent from the following detailed specification when read in conjunction with the accompanying drawings.

BRIEF DESCRIPTION OF THE DRAWINGS

FIG. 2 depicts a cross-sectional schematic view of the intensity distribution of light beam produced by a first illumination means.

FIG. 3 depicts a cross-sectional schematic view of the intensity distribution of the light beam of FIG. 2 following its divergence.

FIG. 4 depicts a cross-sectional schematic view of the intensity distribution of the light beam of FIG. 3 following its convergence.

FIG. 5 depicts a plot of the intensity versus distance of the light beam cross section of FIG. 4.

FIG. 9 depicts a schematic cross-sectional view of light rays being reflected by two different surfaces and being focused by a lens system.

FIG. 10 depicts a perspective schematic view of a portion of the invention used to illuminate objects and measure cross-sectional image dimension.

FIG. 11 depicts a cross-sectional schematic view of two support rollers supporting a cylindrical pellet in a second region of illumination.

FIG. 12 depicts an elevational view of one cylindrical pellet abutted against the ends of two other such pellets.

SUMMARY OF THE INVENTION

Optical inspection in accordance with the invention may be carried out using a first illumination means which produces light of non-uniform spatial intensity and whose intensity distribution may vary with time. The light is diverged by a lens to spread the intensity maxima of the light in a first direction of divergence. A collimating lens reduces the amount of divergence to provide a light beam comprising substantially parallel rays. The light beam is then converged in a direction perpendicular to the direction of divergence to provide a first elongated region of illumination having a substantially uniform intensity distribution despite having been produced by the spatially non-uniform first illumination means. Further, the effect of time variance of the intensity distribution is to shift from one particular intensity distribution to another. Since the lens system described above serves to transform each such distribution into a spatially uniform distribution, the time-variance of the first illumination means merely results in a variance between respective spatially uniform distributions, to no detriment. Thus, a first region of illumination is provided whose incident light intensity is substantially uniform in time and space.

An object present in the first region of illumination reflects light to an array of photosensitive elements. Each element produces an output signal in response which is indicative of surface features of the object at a position on the surface that corresponds to the known position of each respective element. Thus, surface features of the object can be mapped.

The invention further provides a second illumination means which may have nonuniform characteristics like the first illumination means. The light is diverged by a lens and then collimated to provide a second region of illumination of substantially uniform intensity in space and time. An object present in the second region blocks or eclipses the light. The non-eclipsed portion of the light is detected by a second array of photosensitive elements which produce output signals indicative of the size and position of the eclipsed region. Thus, a cross-sectional dimension, such as the height of the inspected object may be measured.

The present invention provides a significant increase in the accuracy of measurement by utilizing large aperture, flat-field relay lenses to focus light from either or both regions of illumination onto either or both photosensitive element arrays.

DETAILED DESCRIPTION OF THE INVENTION

Figure 1:
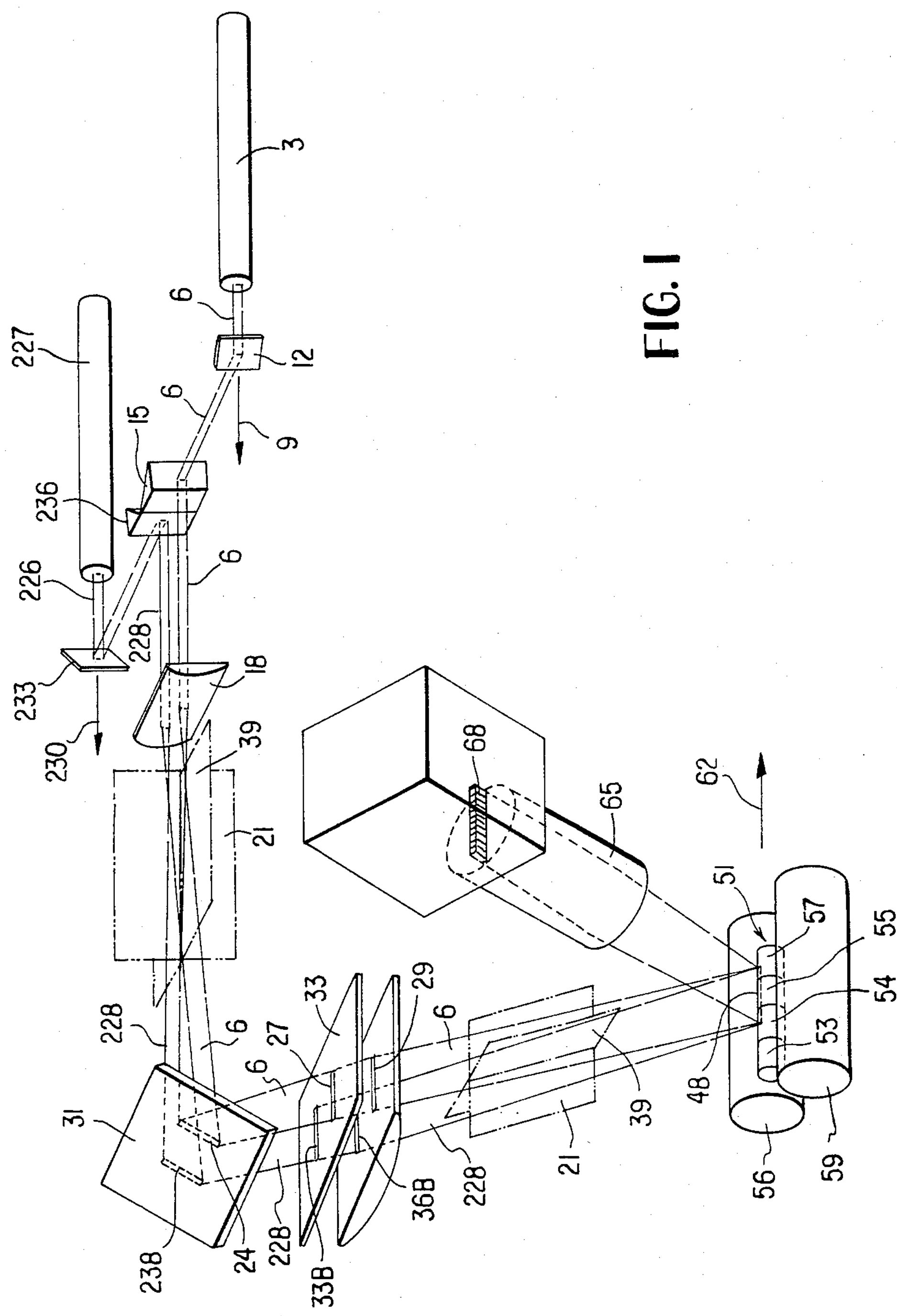
FIG. 1 depicts a perspective schematic view of a portion of the invention used to illuminate objects and detect surface features.

With reference now to the drawings, FIG. 1 illustrates a preferred embodiment of the surface inspection portion of the apparatus which forms the subject matter of the present invention.

As shown, first illumination means, preferably using a multi-mode laser source 3, projects a first light beam 6 in the direction of propagation indicated by arrow 9. The term "direction of propagation", as used herein, refers to the direction in which light beam 6 is projected in any given portion of the beam, as shown. It will be understood that the beam may be redirected by mirrors, prisms, or the like and that reference numeral 6 is used throughout FIG. 1 to designate the beam, regardless of how it is redirected or reshaped.

The direction of propagation of beam 6 is seen to be changed 90° by reflecting means 12, e.g. a mirror. Beam 6 is redirected to a second reflecting means which consists of a prism 15 in the illustrated embodiment. Prism 15 redirects light beam 6 by 90°, so that it travels in a direction parallel to arrow 9 until it encounters a first diverging means in the form of lens 18. Anamorphic lens 18 refracts the light beam 6 and causes it to diverge in a first plane of divergence, as indicated by rectangle 21. As shown, this plane is parallel with the direction of propagation indicated by arrow 9, and located in the plane of FIG. 1. Line 24, which schematically illustrates where beam 6 intersects mirror 31, shows the enlarged beam width at that location. Mirror 31 reflects the now diverging light beam toward a first collimation means in the form of lens 33. Lens 33 refracts light beam 6 to reduce the degree of divergence so that all portions of the light beam are traveling in generally parallel directions. This is schematically illustrated by reference numerals 27 and 29 which designate the intersection of beam 6 with lenses 33 and 36 respectively.

Lens 36 refracts light beam 6 to converge all portions of the beam 6 in directions parallel to a plane of convergence which is schematically indicated by rectangle 39. Rectangle 39 is parallel to the direction of propagation of the beam at that location, and it is perpendicular to the plane of divergence indicated by rectangle 21. Rectangles 21 and 39 are shown at two locations in FIG. 1 to further illustrate the reference directions which the rectangles define. It will be seen that the relatively flat light beam 6 which exits a second anomorphic lens 36 is parallel to the plane of rectangle 21, i.e. it is nearly parallel to the plane of the drawing. Lens 36 further directs and focuses the light beam to form an elongated first region of illumination 48 which has a large length-to-width ratio. This region of illumination, which occupies a portion of a larger viewing field, is illustrated in greater detail in FIG. 4.

Light beam 6 is preferably produced by a multi-mode laser 3, as explained above. Such a laser is utilized for its high output power obtained at relatively low cost and for its more uniform cross-sectional intensity profile as compared with others available at similar cost. Its instantaneous intensity distribution is illustrated by the cross-sectional view of beam 6, shown in FIG. 2. It will be understood that the distribution shown may vary with time because of the multi-mode operation of the laser source. In FIG. 2, intensity maxima are schematically illustrated by circles 115. Regions of lesser intensity are shown by dashed circles 118. The light intensity changes gradually between circles 115 and 118.

Lens 18 causes the light beam to spread out, as previously explained. As shown in FIG. 3, ultimately the spreading causes the points of maximum light intensity to be more uniformly distributed between points 121 and 122, i.e. along the horizontal dimension of illuminated region 48. Lens 36 operates to converge the region of illumination along the vertical dimension, that is, to decrease the height of the cross-sectional view, as shown from a comparison of FIGS. 3 and 4. The result is to provide the region of illumination with a large length-to-width ratio.

The light intensity distribution of region 48 is further illustrated in FIG. 5. Points 121 and 122 in FIG. 5 correspond to the like-numbered points in FIGS. 3 and 4. As shown, the light intensity is relatively uniform throughout. Such time-variance of the intensity distribution of laser source 3 as may occur, e.g. due to multi-mode operation, will cause only slight fluctuations in the distribution of the light beam converging on the region of illumination 48. This is due chiefly to the fact that changes in the laser intensity distribution serve to shift intensity maxima such as 123 in FIG. 5 to new positions such as those occupied by maxima 124 shown as dotted lines. Since the predominant intensity level at all points between points 121 and 122 is that of dotted line 125 and since the intensity maxima 123 or 124 add only small increments of intensity such as that indicated by the incremental distance 126, the shifts in position of intensity maxima 123 do not appreciably alter the predominant level of base line 125.

In the preferred embodiment of the invention shown in FIG. 1, lens 36 projects the first region of illumination onto a stack 51, which is shown as including cylindrical pellets 53, 54, 55 and 57. Although the stack will normally contain a larger number of pellets, those shown are adequate for the discussion herein. The stack is supported by a pair of rotating rollers 56 and 59.

In operation, pusher means, not shown, will cause stack 51 to advance in the direction shown by arrow 62. The rotational motion of rollers 56 and 59 is imparted to stack 51 and combines with the translational motion imparted by the pusher means to cause the stack to spiral about its own axis. As a consequence, illuminated region 48 sweeps the surface of stack 51 along a helical path as the stack rotates and advances in the direction of arrow 62. Light reflected from the illuminated stack suface region is collected by lens 65, which focuses the light onto a light detector 68 in the form of a linear array of photosensitive elements. Each photosensitive element receives reflected light from a corresponding sub-region of illuminated region 48. The amplitude of the output signal provided by each element will correspond to the amount of light reaching the element at any given instant.

The light projected onto the photosensitive elements of array 68 contains information concerning the surface features of the pellets of stack 51 which have entered region 48. In the discussion which follows, converging light beam 6 is treated as comprising many incident light rays, all traveling in relatively parallel directions.

Figure 6:
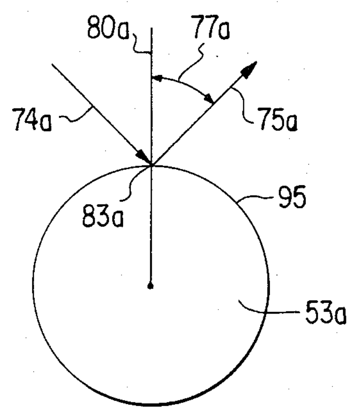
FIG. 6 depicts a schematic cross-sectional view of a light ray being specularly reflected by a smooth, shiny cylindrical surface.

FIG. 6 illustrates a pellet 53 upon which a light ray **74*a* is seen to be projected. Assuming pellet 53*a* to have a shiny surface, incident light ray 74*a* will be specularly reflected as shown. The reflected ray, designated 75*a* in FIG. 6, travels at an angle 77*a* with respect to a reference line 80*a*. The latter is normal to the pellet surface, i.e. it is perpendicular to a tangent of the pellet surface at the locus of reflection, the latter being designated 83*a* in FIG. 6**.

Figure 7:
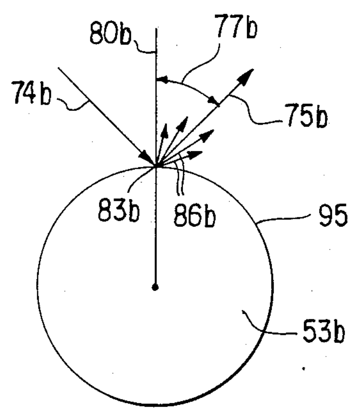
FIG. 7 depicts a schematic cross-sectional view of a light ray being diffusely reflected by a smooth, dull cylindrical surface.

FIG. 7 is similar to FIG. 6 but illustrates the situation for a pellet **53*b* which has a dull surface. Pellet 53*b* reflects less light at an angle 77*b*, even though incident light ray 74*b* is identical to ray 74*d*. Additional light is difusely reflected in random directions, as indicated by reflected rays 86*b***.

Figure 8:
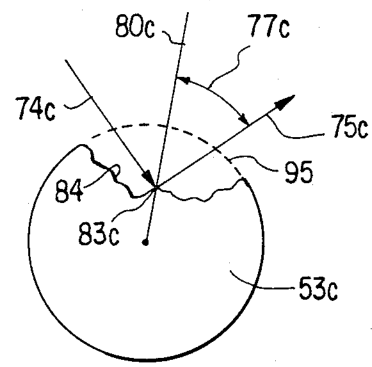
FIG. 8 depicts a schematic cross-sectional view of a light ray being reflected from a greatly exaggerated pit in a cylindrical surface.

FIG. 8 illustrates pellet **53*c* which has a rough surface. As indicated in exaggerated form at 89, the pellet surface is pitted in the illustrated example. Incident light ray 74*c* produces reflected ray 75*c* at a random locus of reflection 83*c*. Specifically, there will be a plurality of loci of reflection for the respective light rays which constitute the incident beam and these loci may be located anywhere within pit 89. Accordingly, reflection angle 77*c* will also have a random size, i.e. it may be smaller, larger, or the same as angle 77*a* or 77*b*. Hence, incident light ray 74*c* will be reflected in several random directions. Thus, the reflection pattern of rays 75*b* from a dull surface and of rays 75*c* from a pitted surface can be similar. Both are schematically represented within the area enclosed by dotted line 92 in FIG. 7. Since a portion of the cylindrical surface is missing where there is a pit, as shown in FIG. 8, the locus of reflection in such a situation is not located on the ideal cylindrical surface 95, as is the case in FIGS. 6 and 7**.

The first illumination means in FIG. 1 comprises multi-mode laser 227 in addition to multi-mode laser 3 described above. The lasers can be operated alternately or together. Alternate operation can provide longer life between maintenance inspections by using one laser until it malfunctions and then replacing it with the other. When used together, the lasers can provide a first illumination region of greater intensity than is possible with a single laser.

Second laser 227 is positioned in a symmetrical fashion to the first laser. That is, it projects a beam of light 228 in a direction of propagation indicated by arrow 230. Reflecting means, such as mirror 233, reflects the light beam to another reflecting means such as prism 236. The latter projects the light beam to first diverging means 18 which diverges the light and causes it to fan out in directions parallel to plane 21. Mirror 31 reflects light beam 228 at points shown by dotted line 238 to the aforesaid first collimation means, i.e. as lens 33. Light beam 228 intersects lens 33 at points shown by dotted line **33*b*. Lens 33** reduces the degree of divergence of the beam. The rays of the resultant light beam all travel in relaively parallel directions.

Light beam 228 exits lens 33 and then intersects lens 36 at points indicated by dotted line **36*b*. Lens 36 converges all portions of light beam 228 in directions parallel to plane 39, which is perpendicular to both the direction of propagation of light beam 228 as well as to the direction of divergence. Accordingly, light beam 228 is diverged in one direction perpendicular to the direction of propagation and is converged in a direction perpendicular to both the directions of divergence and of propagation to provide an elongated region of illumination having a large length-to-width ratio. This region of illumination, produced by light beam 228, coincides with that produced by light beam 6 to produce the aforesaid first region of illumination 48, shown in greater detail in FIG. 3**, which as a substantially uniform light intensity distribution.

In a preferred embodiment of the invention, optical means 65 comprises a lens system which acts as a large-aperture, flat-field relay lens. Such a lens serves to collect much of the light reflected from a point such as **83*b*, irrespective of whether the light is reflected substantially in a single direction, as from a shiny surface, or in many random directions, as from a dull surface. This manner of collection is schematically illustrated in cross section in FIG. 9, which depicts selected superimposed portions of FIGS. 7 and 8. Lens system 65, which includes lens element 101, collects rays 75*b* and 75*c* and focuses them upon focal plane 104. Rays 75*b*, which are reflected from the locus of reflection 83*b* on surface 95, are seen to be focused on array 68 of photosensitive elements which is located in focal plane 104. By contrast, rays 75*c* which are reflected from locus 83*c* located at the floor of a pit, are focused upon point 107. The latter is likewise located in the focal plane, though displaced from array 68. Thus, lens system 65 functions to distinguish between randomly directed rays, such as rays 75*c* which are reflected from a locus that is displaced from the ideal surface 95, and randomly directed rays such as 75*b*, which are reflected from a point on surface 95. The distance between point 107 and array 68 is indicative of the amount of displacement of locus 83*c* from surface 95. Accordingly, output signals produced by the photosensitive elements of array 68 indicate the degree to which the surface of pellets 53 conforms to a predetermined configuration, such as that of surface 95**.

It will be clear that the amount of light collected by lens 65 is relatively independent of whether the pellet reflecting the light is shiny as in FIG. 6, or dull as in FIG. 7. In both cases, those reflected light rays which have angles of reflection generally indicated at **77*b* and 77*c*, such that the rays strike lens element 101 within its periphery, 110 will be collected. They are then focused upon photosensitive array 68 more or less accurately, depending upon the degree of dislocation of locus 83*c* from surface 95**. Thus, the amount of light focused upon an individual photosensitive element from an individual sub-region is relatively independent of the degree of scattering and hence of the reflectivity of the pellet surface.

In a preferred embodiment of the invention, array 68 has 1024 photosensitive elements. Each element "views" a small portion (sub-region) of the region illuminated by the incident light beam. The output signals produced by the photosensitive elements are transmitted to data processing circuitry (not shown) which is capable of mapping the features of the pellet surface as the latter is helically scanned in the manner discussed above. Such mapping will not only locate isolated pits, but may also determine whether the output signals indicate the existence of an elongated crack in the surface. The processing of the output signals may also determine the total amount of missing surface area, e.g. as a percent of the total pellet surface area. This may serve as a figure of merit concerning the acceptability of a particular pellet upon inspection.

In addition to the aforesaid first region of illumination, designated by the reference numeral 48 in FIGS. 1, 3 and 4, the viewing field further contains a second region of illumination, the latter being illustrated in FIG. 10. FIG. 10 also shows second illumination means, which includes a multi-mode laser source 130 adapted to project a second light beam 131. The initial direction of propagation of the beam is indicated by arrow 132 and it may have a light intensity distribution similar to that shown in FIG. 2. Reflecting means such as mirrors 133 and 136 redirect beam 131 and project it to a divergence means in the form of lens 139. This lens serves to refract light beam 131 and to diverge it in a plane parallel to its direction of propagation such as that following lens 139. The latter plane is schematically indicated by rectangle 141. A second collimation means in the form of lens 150 functions to reduce the degree of divergence and to provide a light beam whose cross sectional dimensions remain substantially parallel. Further reflecting means in the form of a mirror 153 reflects the light to a second region of illumination, generally designated by the reference numeral 156, which likewise has a large length-to-width ratio. The intensity distribution of the light projected onto the second region of illumination resembles that shown in FIG. 3.

An object under examination, such as the cylindrical pellet 53 in FIG. 10, will eclipse or block out part of the beam 131. The eclipsed part of the beam is designated 157 in the drawing and is located between a pair of transmitted parts 159 and 162 of the beam. The transmitted parts of light beam 131 are projected onto mirror 165 and thence redirected to a second lens system 168. In a preferred embodiment of the invention the latter comprises a lens system consisting of a number of lens elements. Rollers 56 and 59 each contain a slit 171 to allow the lower part of light beam 131, i.e. part 162, to travel unimpeded beneath the pellet.

Lens system 168 acts as a large-aperture, flat-field relay lens, similar to that previously discussed in connection with lens system 65. This lens system is focused upon the plane perpendicular to FIG. 11 and indicted by the centerline passing through points 221 and 221A.

This focusing assists in capturing light which is diffracted at these points and which would otherwise blur the image of eclipsed portion 171 projected onto array 174. This lens system serves to focus parts 159 and 162 of light beam 131 onto a detector 174. In a preferred embodiment of the invention, detector 174 comprises a linear array containing 1024 photosensitive elements. Each element corresponds to a sub-region of the region of illumination designated 156. Transmitted light from region 156, which is projected onto the elements of array 174, provides information concerning the dimension of the blocking object which is transverse to the light beam. In the case of pellet 53, the distance between parts 159 and 162 of the beam is a measure of the pellet diameter in the region of illumination 156. This distance is designated by reference numeral 177 and it is manifested on the photosensitive elements as a region 180 which is not illuminated. Data processing circuitry (not shown) may be used to process the output signals generated by array 174 and to automatically compute the pellet diameter. Further, information relevant to the determination of whether the pellet 53 conforms to a perfectly cylindrical standard is obtained by measuring the diameter variation as pellet 53 rotates around its own axis. A substantially constant diameter indicates a high degree of roundness, i.e. adherence to the standard.

FIG. 11 schematically shows a portion of the apparatus of FIG. 10 in cross sectional view, the cross section being taken through the roller slits, and illustrates further the apparatus and procedure for determining pellet roundness. As explained above, roller 56 contains a slit 171 which extends inward from roller surface 183 to surface 186 of the roller shaft. Likewise, slit 171A in roller 56 extends inward from roller surface 183A to shaft surface 186A are positioned such that they support pellet 53 at points 189 and 192, respectively. A reference marker such as knife edge 204 is positioned to provide a reference point 207. Pellet 53 is assumed to rotate in the direction of arrow 222. Light beam 131 is defined between upper edge 208 and lower edge 209. It is projected in the direction of arrow 240 onto the region of illumination 156, which is shown schematically in the drawing. As previously explained, rollers 56 and 59 are slotted in the vicinity of region 156, down to central cores 186 and 186A respectively, so as to admit the full height of beam 131. Pellet 53 eclipses part of beam 131. The eclipsed transverse dimension 177, intermediate transmitted beam portions 159 and 162, is defined by upper and lower edges 214 and 215. In the absence of knife edge 204, beam 131 would appear in two parts to the left of pellet 53: Part 59 having upper and lower edges 208 and 214 respectively, and part 162 having upper and loer edges 215 and 209 respectively. However, the presence of knife edge 204 eclipses part of beam 131 near lower edge 209, to define new lower edge 213 of transmitted beam part 162.

Transmitted beam parts 159 and 162, following optical manipulation by lens system 168, impinge upon the photosensitive elements of array 174. As previously explained, the output signals produced by these elements contain information from which transverse distance 177 can be determined. Similarly distance 218, which is defined by edges 213 and 214, can be determined in this manner. Any change in these two distances as pellet 53 rotates in the direction of arrow 222 indicates a deviation in pellet roundness.

In a preferred embodiment of the invention, opposite ends of each pellet are preferably chamfered. This is illustrated in FIG. 12 where pellet 54 is shown in side view with its chamfered facets 225 and 226. As shown in the drawing, the chamfer enhances the boundary between pellet 54 and adjacent pellets 53 and 55. It will be clear from the discussion of FIG. 11 that the transverse dimension 177 will shrink in size when chamfered pellet portion enters the region of illumination 156. This occurs as the pellet stack moves in a direction normal to the plane of FIG. 11 and brings the reduced diameter of the chamfered portion into the viewing field. The change will be detected by the output signals of array 174 on which additional elements are now illuminated. The signal variation may be used to indicate the beginning (or the end) of a pellet and hence it also lends itself to counting the number of pellets that pass through region 156 and to measure pellet length if the linear pellet velocity is known.

It will be clear that the length of the light paths illustrated in FIGS. 1 and 10 are determined by the optical characteristics of the various lenses used, which in turn are selected in accordance with the optical effects that are desired. In order to contain each light path in a volume of relatively small size, the various mirrors and prisms are shown which redirect the light beam as necessary. Thus, the actual distance between the light source and its corresponding region of illumination is considerably shorter than the path of the redirected light beam so as to allow the apparatus to be installed within a housing of relatively small size.

The invention disclosed herein provides first and second regions of illumination in which the light intensity is substantially uniform, notwithstanding the fact that spatially non-uniformn and generally time varying light sources are employed. Thus, less costly light sources, such as multi-mode lasers, may be used. The light beams are projected to the respective first and second regions of illumination. In these regions, objects to be inspected for surface features reflect light. Objects examined for dimensional conformance eclipse part of the light beam. The use of lenses which collect a large portion of the light directed to the arrays minimizes light loss and allows the use of less costly low intensity light sources. These lenses focus the light onto arrays of photosensitive elements which then provide signals indicative of the aforesaid surface features and dimensional features.

While a preferred embodiment of the invention has been disclosed, various modifications may be made to adapt the invention to different requirements. For example, although laser sources have been disclosed, the use of incandescent light sources is feasible in situations where coherent light is not a primary requirement and where the generated heat can be tolerated. Similarly, the manner in which the light beam is redirected by the use of mirrors and prisms may be varied to suit a particular situation. Where compactness is unimportant and a substantially linear light path can be accommodated, the mirrors and prisms may be dispensed with completely.

Although a photosensitive element array has been disclosed as a detector, it will be clear that a scanning electron detector, such as a television camera, could be employed.

As explained above, the use of a large-aperture, flat-field relay lens provides high efficiency in the collection of light, as well as providing accurate focusing. Certain applications may not require these features and hence a different, and possibly less expensive, lens system may be substituted.

The invention is not limited to the inspection of cylindrical pellets and may be extended to the examination of objects having a different geometry, as well as to the inspection of different features. Thus, while apparatus to determine characteristics of reflected and eclipsed light beams projected onto objects has been disclosed, the invention is similarly applicable to the inspection of light-transmissive objects. For example, opacity measurements may be carried out wherein the light beam is diminished in intensity by a transparent or translucent material rather than being blocked. In such a case, the spatial intensity distribution of transmitted light through the material may be compared to that of light transmitted through a reference material.

While a preferred embodiment of the invention has been disclosed, it will be clear that the invention lends itself to numerous modifications, variations, substitutions and equivalents and that certain disclosed features may be used without the use of other such features. All of these changes will be obvious to those skilled in the art and are embraced within the invention herein. Accordingly, it is intended that the present invention be limited only by the spirit and scope of the appended claims.

What is claimed is:

1. Apparatus for the optical inspection of the surface, the diameter, the roundness and chamfer of each of a succession of substantially cylindrical, coaxially contiguous pellets spiraling about a common axis while advancing through a viewing field;

said apparatus comprising:

first illumination means effective to project at least first and second laser beams in a first direction of propagation;

a first anamorphic lens effective to diverge said first and said second laser beams in a first divergence plane substantially parallel to said first direction of propagation;

first collimation means effective to reduce the amount of divergence of said laser beams in said first divergence plane;

a second anamorphic lens effective to converge said first and second laser beams in a direction substantially perpendicular to said first divergence plane, said second anamorphic lens being further effective to confine said beams to a first elongate region of illumination having a large length-to-width ratio on the surface of the pellets under examination;

first detector means including a linear array of first photoresponsive elements and a large aperture, flat field relay lens which directs light to said first elements, each of said first elements being adapted to provide an output signal representative of the amount of light reflected thereto, the light received by said first elements being reflected by corresponding subregions of said first region of illumination on the surface of the examined pellet, said first elements being positioned to receive reflected light only when the angle and the locus of reflection respectively within the corresponding sub-region remain within predetermined limits;

second illumination means effective to project a third laser beam in a second direction of propagation;

a third anamorphic lens effective to diverge said third laser beam in a second divergence plan substantially parallel to said second direction of propagation;

second collimation means effective to reduce the amount of divergence in said second divergence plane and to direct said third laser beam to a second region of illumination, said second region being an elongate area, with large height-to-width ratio, intersecting the whole diameter of each of said pellets in succession;

second detector means including a linear array of second photoresponsive elements each adapted to provide an output signal representative of the amount of transmitted light from said third laser beam incident thereon, said examined pellet occupying a portion of said second region of illumination between said second illumination means and said second detector means so as to eclipse part of said third laser beam and causing two disconnected portions of said third beam to be directed to said second elements;

whereby said first, second and third laser beams each have a substantially uniform spatial intensity distribution and whereby said first output signals are representative of the condition of the surface of the examined pellet and said second output signals are representative of at least the diameter of said examined pellet transverse to said third laser beam.

* * * * *